United States Patent [19]

Abele

[11] 4,362,058
[45] Dec. 7, 1982

[54] ULTRASONIC DIAGNOSTIC APPARATUS

[75] Inventor: Manlio Abele, Garden City, N.Y.

[73] Assignee: New York University, New York, N.Y.

[21] Appl. No.: 200,568

[22] Filed: Oct. 24, 1980

[51] Int. Cl.³ .................................................. G01N 29/00
[52] U.S. Cl. ...................................... 73/599; 128/660
[58] Field of Search .................. 73/599, 600, 618, 620, 73/632; 128/660

[56] References Cited
U.S. PATENT DOCUMENTS

| | | | |
|---|---|---|---|
| 3,609,675 | 9/1971 | Abelle | 333/240 |
| 3,675,128 | 7/1972 | Abele | 333/240 |
| 3,858,437 | 1/1975 | Jarzynski et al. | 73/599 |
| 4,011,747 | 3/1977 | Shaw | 73/620 |

Primary Examiner—Stephen A. Kreitman
Attorney, Agent, or Firm—Daniel M. Rosen

[57] ABSTRACT

An ultrasonic probe for propagating an ultrasonic surface wave which is constrained along the probe with the evanescent pressure field penetrating the subject in a direction orthogonal to the axis of the probe. The ultrasonic probe may then be placed about a plurality of orientations, passing the evanescent pressure field through the subject along the plurality of orientations and detecting the loss of energy in each successive pressure field propagation. A data processing system for processing and correlating each successive detected energy loss in each propagation direction can produce a resultant computed tomographic image of a defined plane through the subject.

19 Claims, 14 Drawing Figures

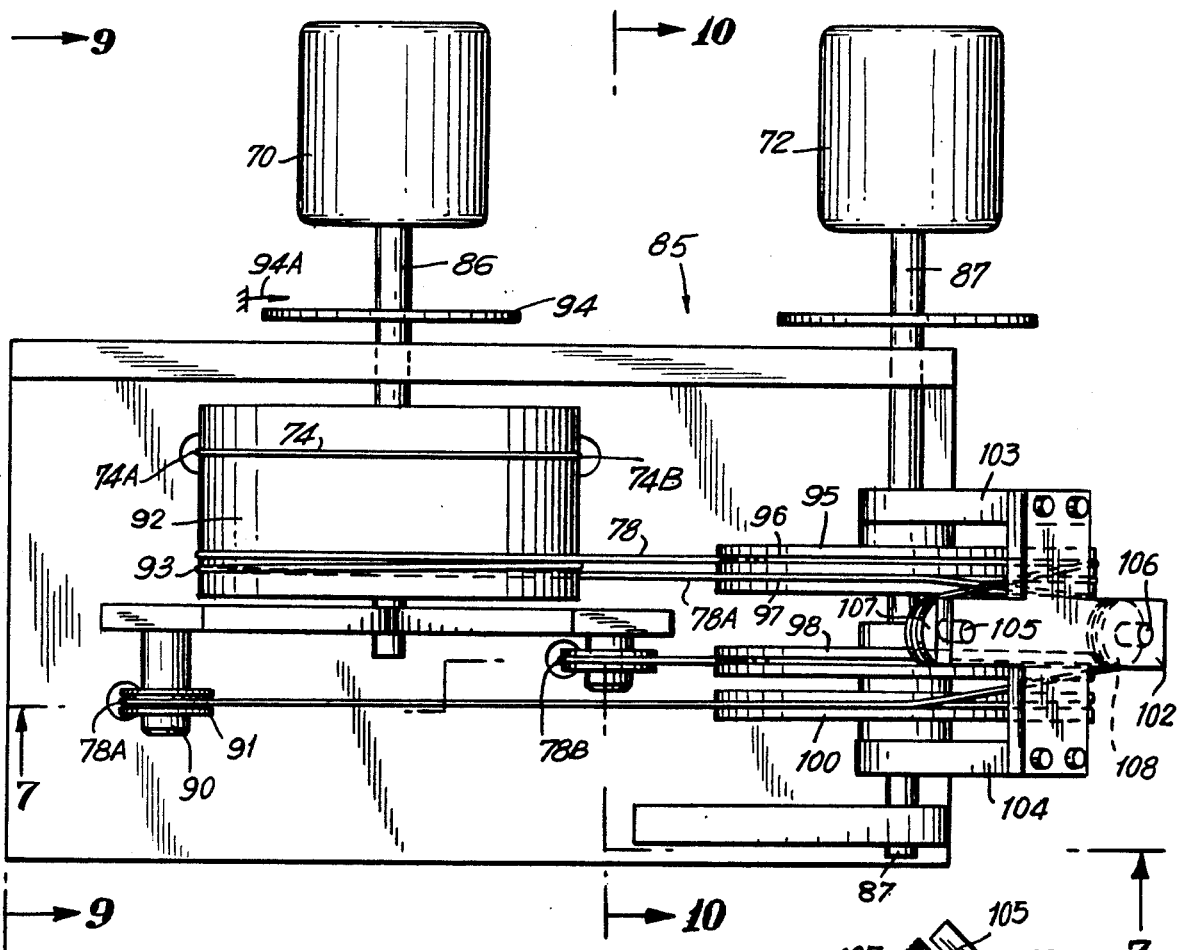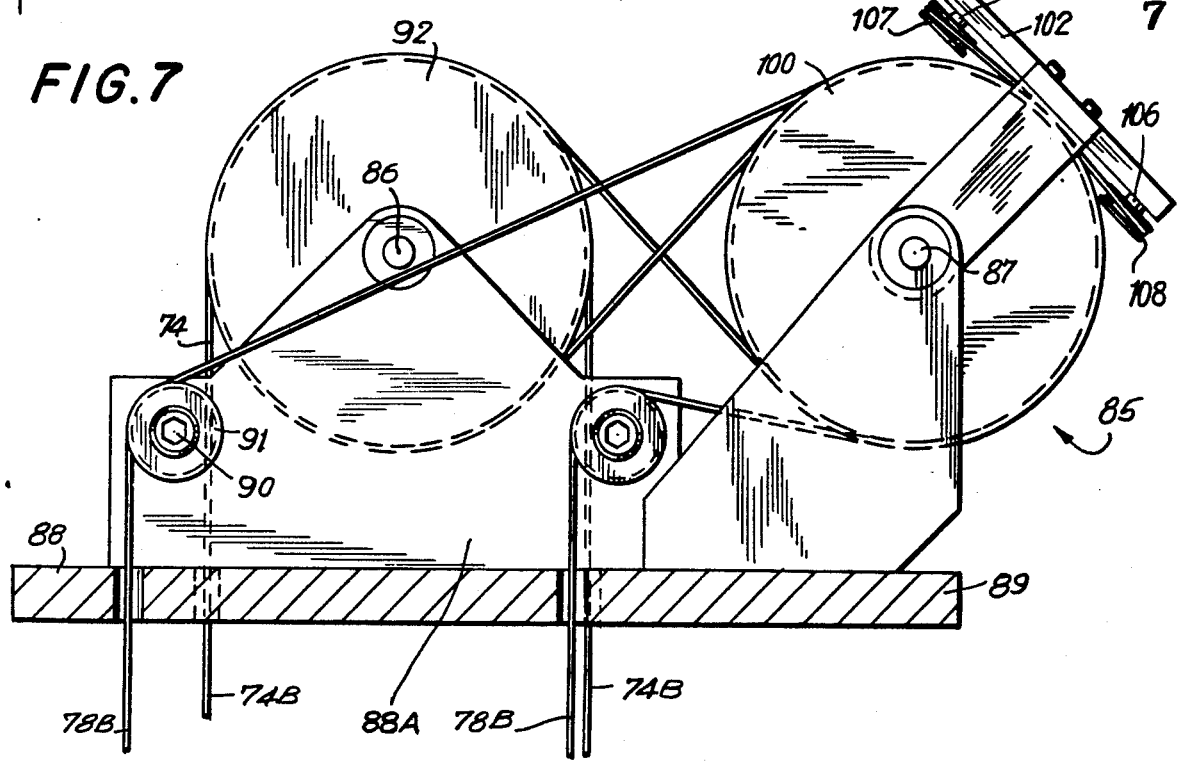

ULTRASONIC DIAGNOSTIC APPARATUS

The use of ultrasound for diagnostic purposes is a conventional and well-known technique. Typical prior art systems utilizing ultrasound employ a form of radar technology transmitting ultrasonic beams from a suitable ultrasonic probe toward a subject to be examined such as a living body. The basis of operation of this system is a measurement of back scattered radiation. Properties like phase shifting of the reflected signal, attenuation and dispersion and effects of local fluctuations of the speed of sound within tissue, as well as effects of side lobes in the radiation pattern, contribute to the complexity of the reflected field.

The resulting images are processed for display on a CRT by utilizing the reflected electrical signal to modulate the brightness of the CRT display. By making the sequential shift of the ultrasonic beams synchronous with the scanning line shift of the electron beams in the CRT, a tomographic image of the living body region is displayed on the CRT. Such a display mode is called B-mode display. To examine an entire cross-section, it is necessary to obtain a plurality of B-mode images at specified intervals for permitting a physician to diagnose an effected region on the basis of the B-mode images taken. Thus, ultrasonic echoscopy may be used to produce displays resembling anatomical cross-sections which are clinically useful when certain qualitative information concerning physical dimensions from various echo pulses provide desired information. Ultrasonic echography has proved a particular value as diagnostic aides in various areas of living tissue involving relatively soft tissue with little bone and air, particularly, the breast, abdomen, pregnant uterus, eye, brain, lungs, kidneys, liver and heart. One disadvantage of ultrasonic echoscopy involves the amount of time necessary to take a scan which will provide a cross-section of the body with a resolution desired for a particular diagnostic technique. The use of hard X-rays, such as in the field of computer aided tomography, while providing more quantitative information about tissue properties and a faster time to complete a body cross-section scan, involves the use of relatively hazardous media, such as the X-ray itself, thereby preventing its use on many of the soft tissue areas noted above. Where safety of measurement media is concerned, the ultrasonic system, if applicable, is preferable to the use of X-ray radiography. It is therefore desirable to be able to provide an ultrasonic system with the resolution and image capability normally found in computer aided radiographic scanners. Various prior art methods to improve resolution capability have been proposed, such as in U.S. Pat. Nos.: 4,186,747, 4,070,905, 3,936,791, 3,881,466, 4,011,747 and 4,157,665. In all these patents however the emphasis is upon improving the resolution of the quality of the image received by the reflected beam in either the A or B type mode scan in ultrasonic measurement. In all of these systems, the reception must provide for compensation of phase shifts of the back scattered radiation, compensating for side lobes in the radiation pattern, and providing for compensation of the effects of local fluctuation of the speed of sound within tissue, or other means required in the general technology of propagation in the ultrasound frequency range and back scattered reflections.

SUMMARY OF THE INVENTION

It is the object of the present invention to provide an ultrasonic diagnostic apparatus wherein energy absorption may be measured by a pure amplitude loss without the necessity for compensating for phase shift and other effects of back scattered radiation.

It is another object of the present invention to provide a processing system in conjunction with an ultrasound transducer which will generate a complex cross-sectional image of the section under scan in a relatively small amount of time and with a relatively high degree of resolution.

In accordance with the foregoing objects, the present invention provides an ultrasonic probe for propagating an ultrasonic surface wave which is constrained along the probe with the evanescent pressure field penetrating the subject in a direction orthogonal to the axis of the probe. The ultrasonic probe may then be placed about a plurality of orientations, passing the evanescent pressure field through the subject along the plurality of orientations and detecting the loss of energy in each successive pressure field propagation. A data processing system for processing and correlating each successive detected energy loss in each propagation direction can produce a resultant computed tomographic image of a defined plane through the subject.

The probe itself may comprise a cylindrical wave guide, containing an acoustic medium, and a transducer oriented to propagate a surface wave within the cylinder. The surface wave mode is such that energy therefrom may be detected by a second transducer or reflected by a reflector located at the other end of the surface wave guide. As a result, any energy loss encountered in the detected wave is purely an amplitude loss or attenuation from scattering or absorption at objects located within the evanescent pressure field surrounding the surface wave guide. Since the scattered energy is basically a free propagation field, no energy will be coupled back into the guide and therefore no phase effects will be realized. As a result, only a pure amplitude loss will be encountered in the probe.

It is also possible to generate an evanescent field by means of a phased array comprising a sequence of adjacent transducers. If the phase difference between adjacent transducers is large enough such that the wavelength measured along the axis of the array is smaller than the wavelength of the frequency involved, no radiation occurs in a direction perpendicular to the phased array, and only an evanescent field is generated.

Processing systems employed to correlate the data achieved from scanning along a plurality of orientations can be the same system conventionally employed in computer aided tomography systems employing radiation scanners. The amplitude decrease measurements are equivalent to beta losses in such systems, and an example of such a system is in applicant's previously filed application Ser. No. 118,866, filed Feb. 5, 1980.

BRIEF DESCRIPTION OF THE DRAWINGS

FIG. 7 is a front elevation view of the motor and pulley drive system of FIGS. 1 and 5.

FIG. 8 is a top plan view of the motor and pulley drive system of FIG. 7.

DETAILED DESCRIPTION OF THE PREFERRED EMBODIMENTS

Figure 1:
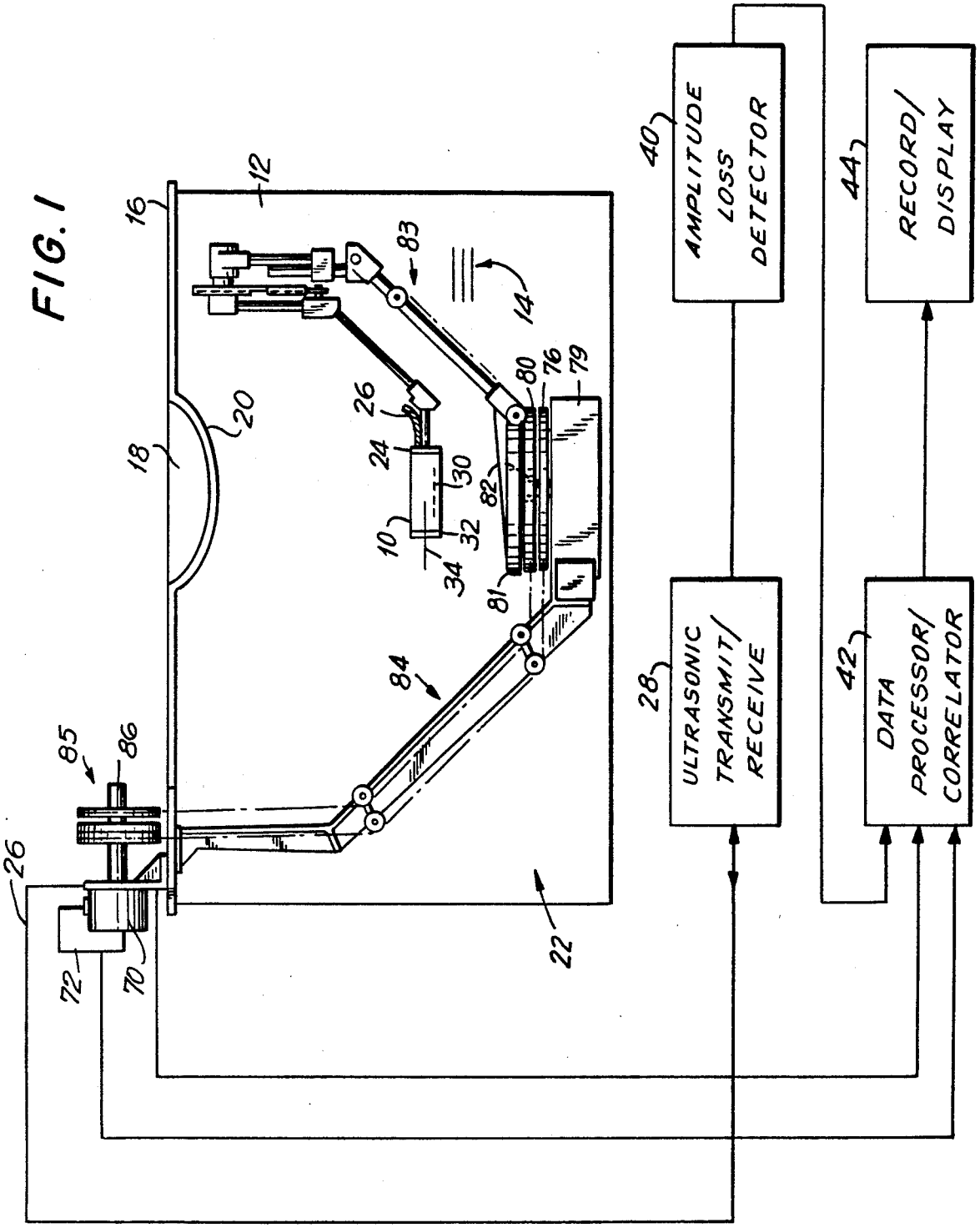
FIG. 1 is a general block diagram of the location of an ultrasonic probe with respect to a subject to be examined, and the connections to a generalized system for performing the analysis in accordance with the present invention.

Referring now to FIG. 1, an ultrasonic probe 10, in the form of a cylindrical wave guide, is located within a tank 12 which is filled with a suitable medium 14 which is relatively transparent to an acoustic wave. A suitable medium, for the transmission of ultrasonic waves, may be a liquid such as degassed water, or an appropriate oil, or sodium chloride solution, or the like. The subject is placed on the tank surface 16 which may be a relatively rigid medium for supporting the subject, such as a table top or the like, and the area of the subject to be examined placed over or into an opening 18. The interface of the liquid 14 with the opening 18 is defined by means of a membrane 20 such as a very thin rubber or vinyl sheet. Since this particular process lends itself well to breast examination, it will be assumed for purposes of this explanation that the subject is placed face down on the surface 16 with the breast area placed into the opening 18 and compressed against the surface of the membrane 20 for examination.

The probe drive mechanism 22, to be explained in further detail below, causes the probe 10 to move about a plurality of orientations with respect to the membrane 20 for purposes of examining the subject area within the opening 18.

The probe 10 is constructed as a cylindrical wave guide. The construction provides a transducer 24 coupled by means of a cable 26 to an ultrasonic transmit and receive driver 28. The driver is of conventional form and serves the purpose of appropriately energizing the transducer 24, for producing a continuous wave signal in the ultrasonic frequency range and measuring the reflected energy received by the transducer 24. The frequency will depend on the penetration desired or attainable. If the frequency is too low, the evanescent field decays too slowly, noise levels increase and the surface wave mode approaches instability. This instability is evident in that the surface wave is no longer guided in the probe, and acts as a free field throughout the medium. As the frequency increases, the field decays more sharply outside the wave guide, and penetration depth decreases. The chosen frequency is thus a tradeoff between penetration depth and stability in the surface wave mode. Thus, for a one to several cm penetration depth, a 0.1 MHz frequency range is approximately correct. The probe 10 is filled with a liquid 30 characterized by a speed of sound lower than the speed of sound in the liquid 14. This construction results in propagation of an ultrasonic surface wave along the longitudinal axis 34 of the ultrasonic probe 10, propagating in a mode whose properties are defined in appendix A. The generation and propagation of the surface wave mode in water focuses sound in a given direction along the longitudinal axis of the probe 10. The probe further includes a reflector 32 located at the opposite end of the cylindrical probe 10. This ultrasound surface wave mode has characteristics similar to those of an electromagnetic surface wave propagation, wherein the propagation is confined to a direction parallel to the axis of the dielectric wave guide, with no loss of radiation in a direction perpendicular to the wave guide axis. Since a radiation field contributing to the loss in the medium does not couple back into the wave guide, the radiation loss results primarily from the amplitude loss with no significant phase shift effects. The surface wave mode is sustained by means of the wave guide formed by the cylinder 10 containing the liquid 30 which exhibits a speed of sound lower than the speed of sound in the liquid surrounding the probe 10, thereby constraining the propagation mode along the axis of the probe 10. Approximately, the amplitude of the pressure wave outside of the cylinder decreases exponentially with the distance from the cylinder. This exponentially decreasing pressure field, termed an evanescent pressure field, propagates along with the surface mode propagation and provides the field wherein the area under examination is penetrated for absorption loss. Hence, for all practical purposes the pressure field is confined within a cylindrical region co-axial with the wave guide and for a given wave guide radius and wave guide medium the dimension of this region may be controlled by proper selection of the frequency of the ultrasound wave. It is also possible to use a wave guide with a transmitter at one end and a receiver at the other end. In this case, the element 24 can comprise the transducing means, and the element 32 comprises the pickup. This arrangement is somewhat simpler, structurally, however the surface wave traverses the guide only once, thus providing a smaller signal differential for detection. It will be understood that in the case of a reflected wave, the probe 10 includes a directional coupler (not shown) to divert the reflected wave to a pick-up. The reflected signal represents twice the total energy loss since the surface wave traverses the wave guide twice.

Two basic properties of this technique make it relevant for ultrasound diagnostics:

1. The advantage of the liquid wave guide as an antenna compared to directional arrays is the elimination of side lobes in the radiation pattern. In addition, the small transverse dimension of this antenna makes it much more suitable to the scanning configurations that conventional arrays or lenses.

2. The liquid wave guide may be used in a scanning configuration wherein the subject to be examined is exposed to the evanescent fields surrounding the wave guide. In spite of the fact that the subject being examined is exposed to a highly non-uniform field, this procedure still provides the required spacial resolution at a distance from the wave guide of the order of two to three times the diameter of the wave guide itself. Further, the guided surface wave mode eliminates many problems associated with free propagation, particularly the effects associated with the local fluctuations of the speed of sound within tissue and the phase shifting effects which must be compensated for in a back scattered radiation mode.

Figure 2:
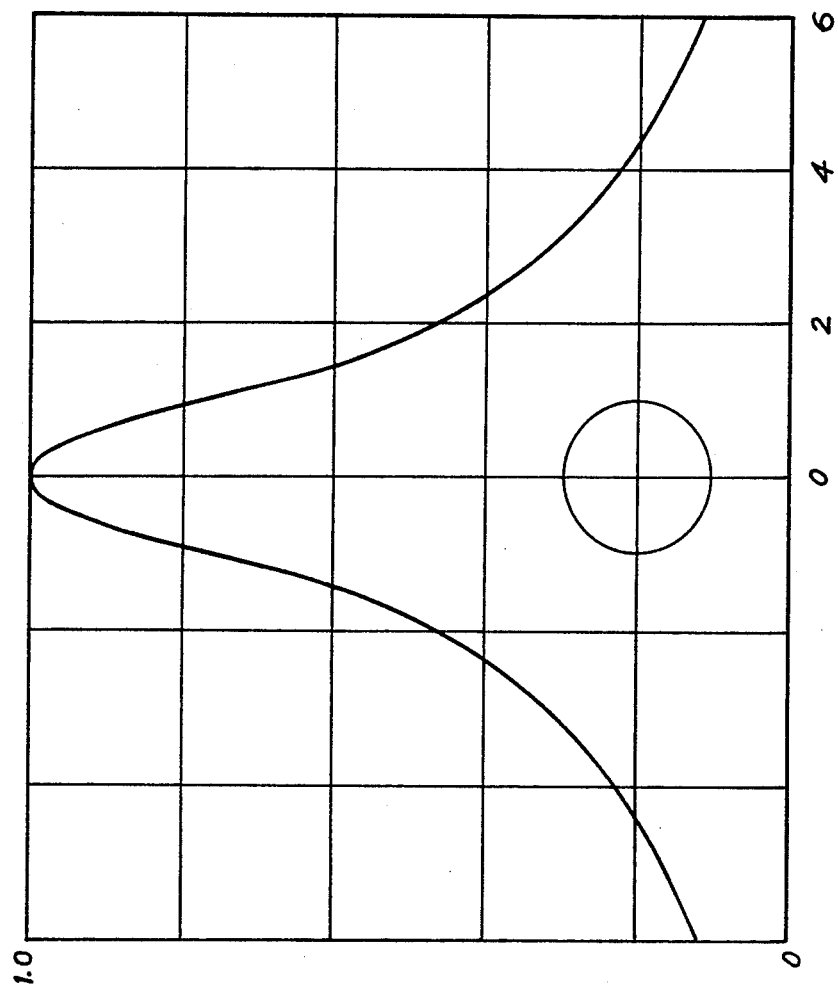

In FIG. 2, the radial distribution of the pressure field relative to the diameter of the cylindrical probe 10 is diagramatically illustrated as an example for one set of parameters relative to that probe. Thus, as shown, the pressure field is at a maximum throughout the internal portion of the wave guide 10, which is assumed to have a unit radius. When the distance from the surface of the probe 10 equals the radius, there is an approximate drop off in the intensity of the pressure field equal to about 50% of the field. When the distance from the surface of the probe is equal to about three times the radius, the intensity of the pressure field is equal to approximately 12% of its original intensity. The nature of the pressure field is evanescent in that there is an exponential decay of intensity as the distance from the surface of the cylinder increases. With a one inch diameter probe, a useful field of about three to five inches from the surface of the cylinder may be realized, at an ultrasonic frequency of 40 KC to 250 KC.

Figure 3:
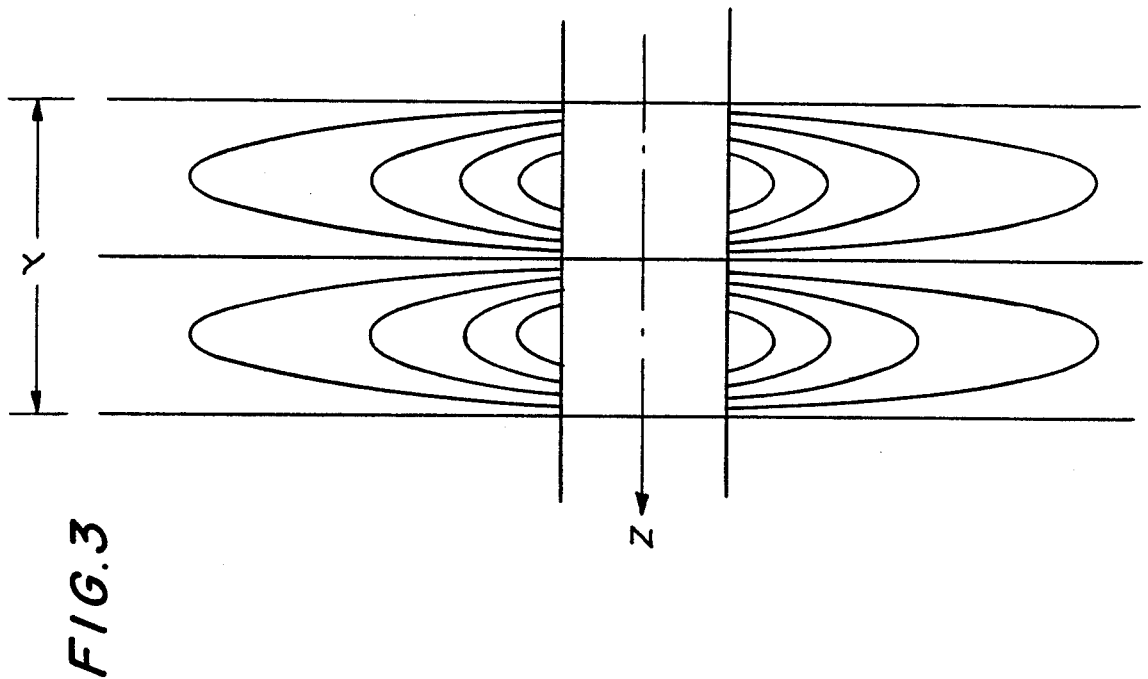
FIGS. 2 and 3 are graphic representations of the pressure distribution fields.

With reference to FIG. 3, it will be evident that at any given instant of time the pressure is uniform throughout the locus of points defined by the equation which controls the surface wave mode. When viewed along the length of the probe, equal pressure lines passing through the subject may be diagramatically illustrated.

Referring again to FIG. 1, as the probe drive mechanism 22 causes the probe 10 to undergo a series of orientations wherein pressure measurements are obtained, each successive propagation causes an amplitude loss. This loss is received by means of the ultrasonic transmit receive driver and receiver 28, and is detected in the amplitude loss detector 40. The loss of amplitude in each successive propagation is correlated with the position of the transducer in accordance with a data processing and correlation circuit 42, and this information is recorded and/or displayed in an appropriate record or display mechanism 44. The data processing and correlation circuits 42 may consist of a general purpose computer, such as is conventionally utilized in computer aided tomography, for storing absorption values relative to their position, correlating such values with other values in other positional areas, and by the use of solving a series of simultaneous differential equations, provide a data pattern corresponding to a cross-sectional image of the section in the area 18 under examination. By assigning gray scale values to each of these data points, a contrasting image may be formed for recording or display in the device 44. The display may be on a cathode-ray tube, or may be provided on hard copy display, as is conventional in computer aided tomography. In addition, the data points may be assigned color values for increasing the optical contrasts of the objects under observation. Since ultrasound techniques are employed, it is possible in successive scans to be measuring the comparative resilience of any objects scanned within the area 18 and to utilize the comparative resilience to indicate a change in resiliency of any anomaly which is measured within a subject area. The use of a change of resiliency may be employed as a diagnostic tool to assist the physician in identifying the quality and nature of the object being detected, without the necessity for intrusive or invasive surgical techniques such as are now conventionally employed.

Figure 4:
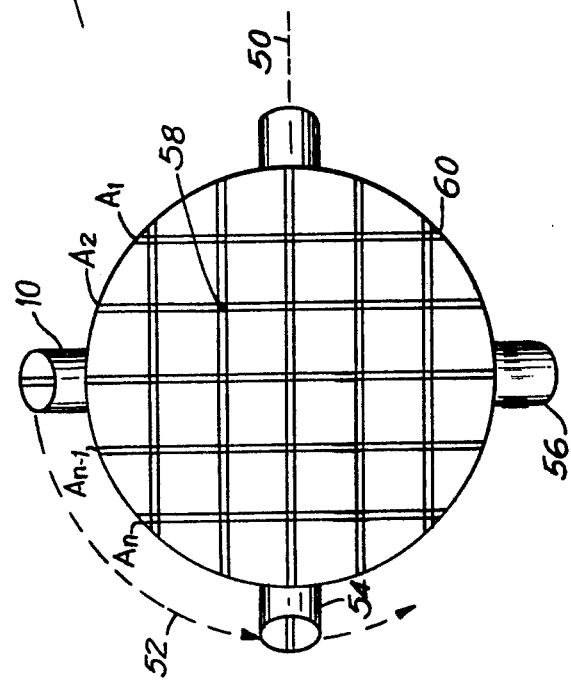
FIG. 4 represents a section of tissue under examination.

Referring now to FIG. 4, the area under examination, as seen in hypothetical cross-section from above in this figure, is scanned by means of the probe 10 along its entire width over a predetermined angle of orientation. During the scan, each successive propagation provides a slice 50 and which is caused by moving the probe 10 in the figure shown from right to left along the angular orientation represented by the series of slices defined as $A_1, A_2, \ldots A_{n-1}$ and $A_n$. These slices are caused by moving the transducer 10 from right to left across the image as shown. The transducer however need not occupy precisely the same angular orientation over its entire transverse scan, but changes its angular orientation by a predetermined amount. For example, the slice represented as $A_1$ may be along an angular orientation of 89° (treating the longitudinal axis 50 through the center of the section as a hypothetical origin axis) with respect to axis 50 and undergo a slow slight skew as moved across the transverse section such that the last section, shown in the figures as $A_n$, is at an angle of 90° with respect to the axis 50. Thus, at the end of the traverse from right to left, the probe 10 may resume its traverse in the opposite direction, making a further series of slices along an angular orientation begining at 90° with respect to the axis 50 and ending at an angular orientation of 91° with respect to the axis 50. This one degree skewing motion can continue from scan to scan along the line indicated by the reference 52 through the position 54 until the probe is once again in the position illustrated as 56, representing a 180° revolution. A 180° revolution will be sufficient to encompass a total scan of the plane represented by the area 18. Assuming a complete circular scan of the area 18 may be made by the probe in one second, a complete scan encompassing 180° of rotation about the object by the probe may therefore be accomplished in 180 seconds, or three minutes. This latter scan speed may be increased by changing the one degree skew to a two degree skew, thereby requiring only 90 scans, thus reducing the total scan time to 90 seconds. Shorter or longer periods may be realized in accordance with the desired resolution of the ultimate image. Since the result will be to provide a plurality of transverse cross-sectional slices through the subject area, each point within the area, such as point 58, will have been traversed by a plurality of beam orientations along a 180° position, thereby allowing the data processing system to provide the series of data points representing individual absorption characteristics of all of the points within the transverse plane 60, for ultimate utilization and display.

Figure 6:
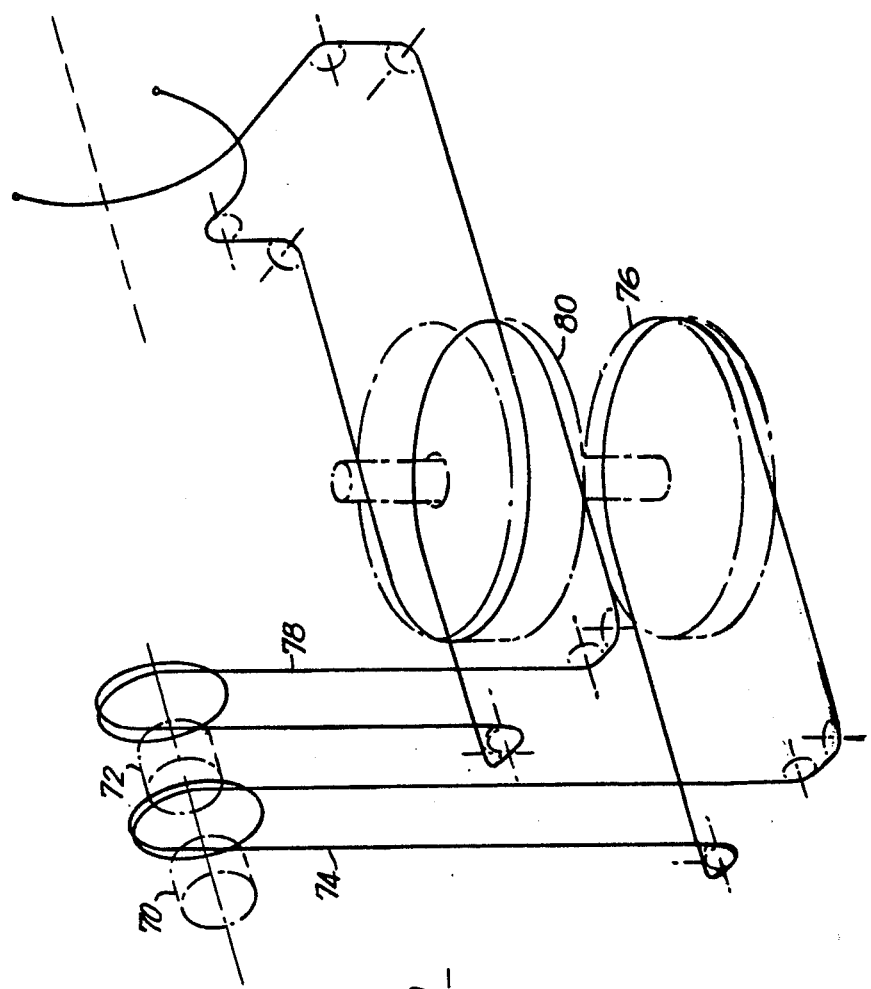
FIG. 6 is a schematic representation of the probe drive system.
Figure 5:
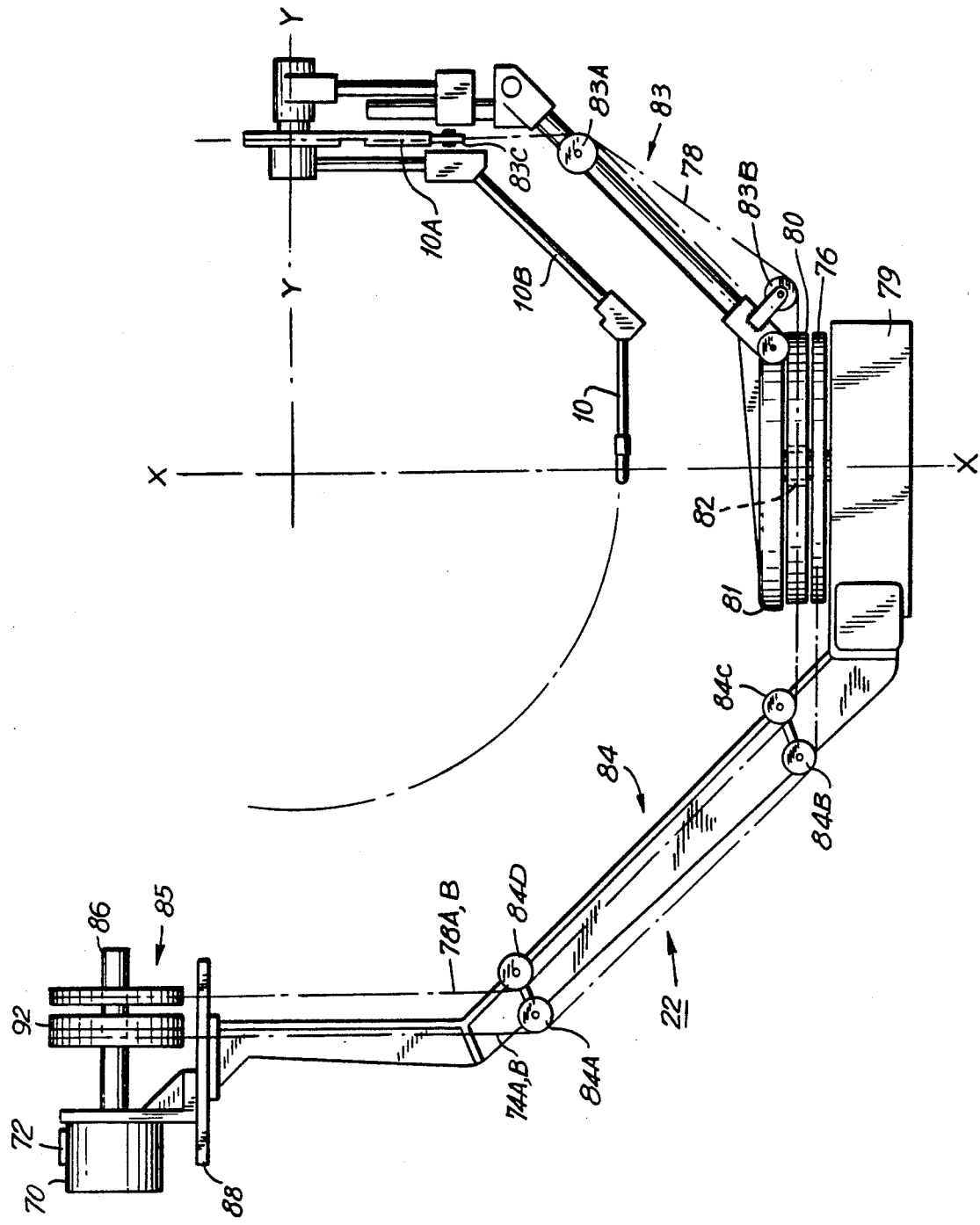
FIG. 5 is a side elevation view of the probe drive system with the tank omitted.

The probe drive mechanism 22 which accomplishes the foregoing action is illustrated in greater detail in FIGS. 5 and 6. The drive mechanism consists basically of two independent drives, including a first motor 70 and second motor 72. First motor 70 is connected through a series of cables 74 through a first turn table 76 which controls the angular rotation of the probe 10 with respect to the rotation about an axis 76. This corresponds to the skew feature noted in the explanation of FIG. 4. This is a relatively slow moving but precise angular orientation control. The other motor, 72, controls a second series of cables 78 and comprises a high speed device for driving the probe about a complete scan of the object area 18. In FIG. 5, the scan would be characterized as a motion into and out of the plane of the paper in the orientation illustrated in the figure. The motor 72 thus drives its respective cable set 78 through a second turn table 80 and which in turn drives the respective control arms through the probe 10 for encompassing a motion about the subject 18 which would correspond to the motion across the plane of the object as shown in FIG. 4.

The preferred embodiment of the probe drive mechanism 22 illustrated in FIGS. 1 and 5 will now be described in greater detail. As will be evident the objective here is to move a probe under the fluid medium in a precise scan pattern as directed by a remote drive assembly outside the fluid area, and to maintain precision control while the probe moves continuously within the tank. In the bottom of the tank 12 is a fixed base part 79 of the probe drive mechanism. A first turntable or drum 76 is mounted on the base part and is freely rotatable thereon; a second turntable or drum 80 is above the first drum and is freely rotatable relative to the base and relative to the first drum. Above the second drum 80 is a rotating platform 81 which is fixed to move the first drum 76 via a splined central shaft 82 or other suitable means. Extending from platform 81 is movable tower 83 for supporting the probe unit 10. The tower 83, platform 81, and lower drum 76 rotate as a unit. Extending from the opposite side of the base 79 is a stationary second tower 84 which extends upward to the motor and pulley drive and control system 85, the latter being secured to the top edge 13 of tank 12. Along both towers 83 and 84 are small idler pulleys 84A-84D and 83A-83C for guiding the control cables as will be described later.

Now consider the front elevation and top plan views, FIGS. 7 and 8 respectively of the drive and control mechanism 85. This mechanism includes two basic shafts designated 86 and 87 which are rotatably mounted in sub-frames 88 and 89 respectively. Shaft 86 is drivable by motor 70 and is bearingly mounted in upright walls 88A of sub-frame 88. Also extending from wall 88A is a stub shaft 90 with an additional idler pulley 91. Fixed to shaft 86 is drum 92 with its pulley grooves 93 around the outer periphery and vernier guide disc 94 indicating the angular position of this shaft 86 and the drum 92 thereon. Parallel to shaft 86 and its drum 92 is shaft 87 with pulley 95 having two grooves 96 and 97, and pulley 98 having one groove 99, and pulley 100 having one groove 101. It should be noted that pulleys 95, 98 and 100 are all freely rotatable on shaft 87; however, also on the shaft 87 is a sub-frame 102 having descending arms 103 and 104 which are fixedly secured to shaft 87 and rotate with it. Extending from sub-frame 102 are shafts 105 and 106 each having an idler pulley 107 and 108 respectively.

Figure 9:
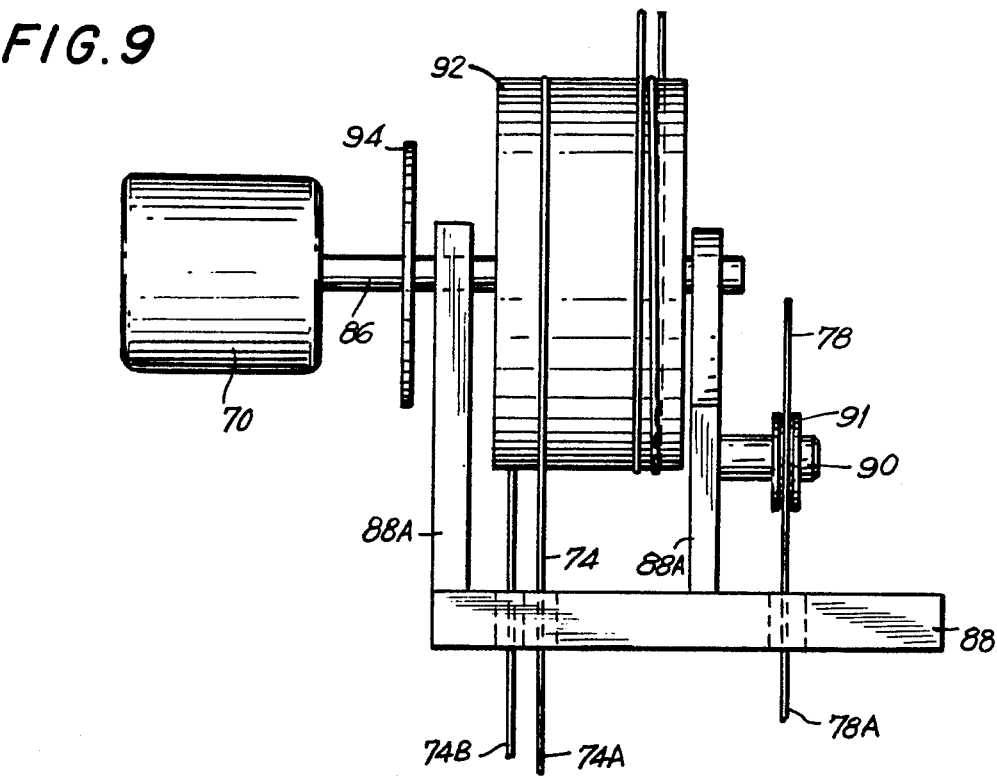
FIGS. 9 and 10 are side elevation views of parts of the system indicated in FIG. 8.
Figure 10:
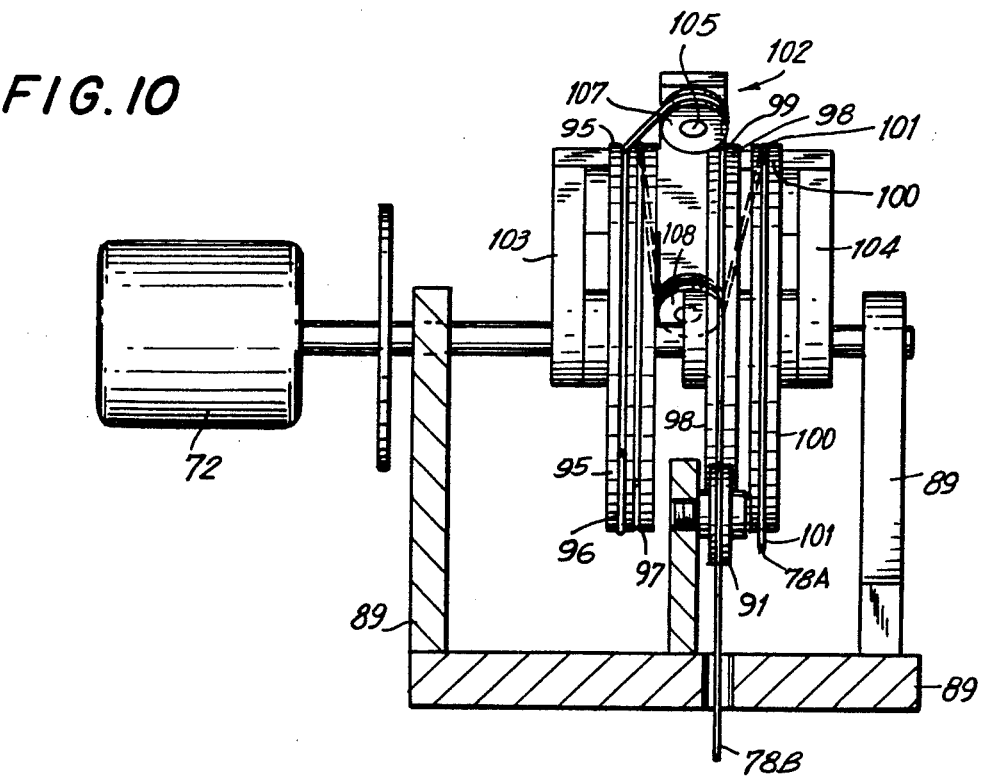
Figure 11:
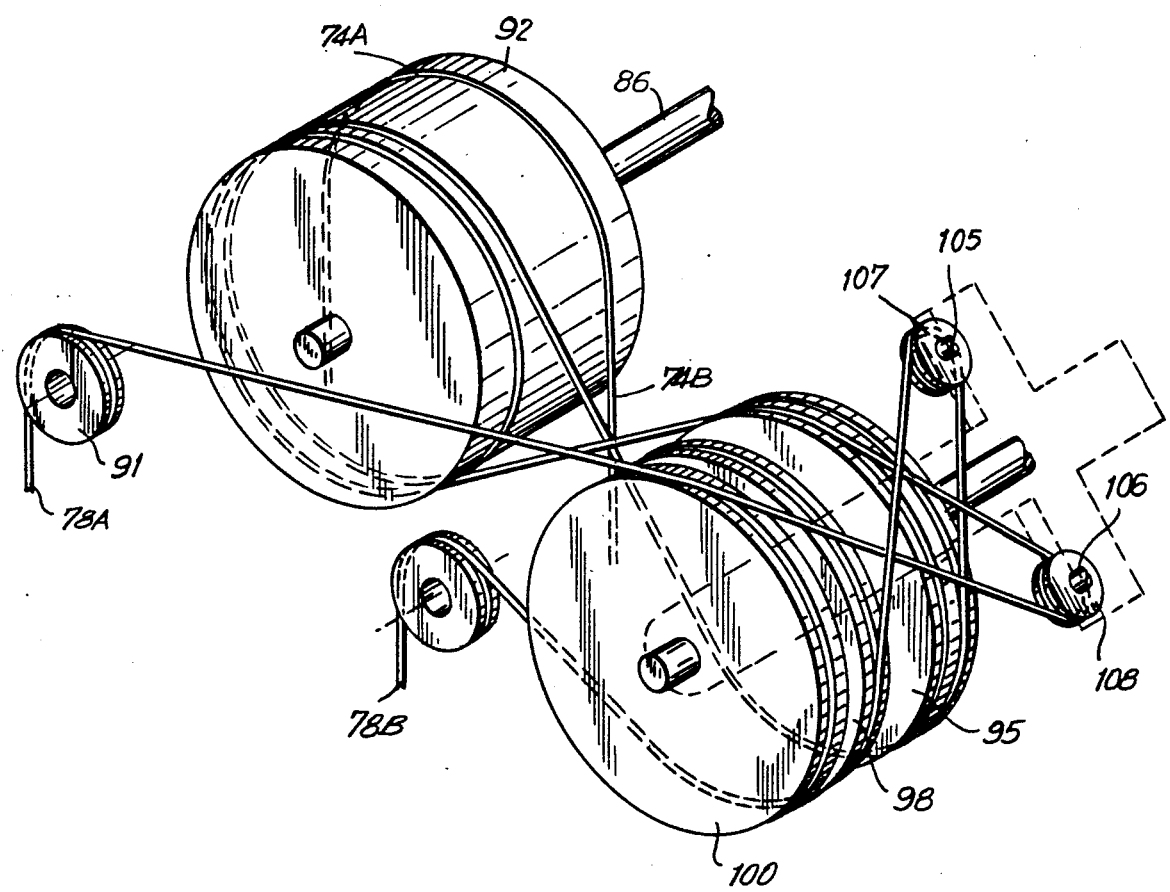
FIG. 11 is a front perspective schematic representation of the cables and pulleys of FIGS. 8-10.

Now consider first cable 74 which extends around drum 92 in the front of FIGS. 8 and 9, and then descends as ends 74A and 74B through support 88 (FIGS. 9 and 5) downward along tower 84 and its idler pulleys 84A and 84B to and around lower drum 76. Rotation of motor 70, shaft 86 and drum 92 causes this pulley cable 74 to directly rotate the lower drum 76 and the upper platform 81 connected thereto, and tower 83 extending upward from drum 76, and the whole probe assembly about vertical axis X—X in the apparatus.

By this arrangement the probe is caused to travel in a circular arc clockwise or counterclockwise about axis X—X. The vernier disc 94 with its pointer 94A provides instant read-out of the rotational position of the probe.

Next consider cable 78 which drives probe 10 to oscillate in an arc about axis Y—Y, essentially independently of the rotary motion of platform 81, tower 83 and the probe about axis X—X.

Despite its circuitous route, cable 78 is basically a loop that extends from motor 72 about drums 95, 98 and 100, down tower 84, around freely rotating idler drum 80, and finally up tower 83 to pivot segment 10A and probe 10 about axis Y—Y. Motors 70 and 72 are operated to slowly rotate platform 81 and the arm 10B carrying probe 10 while independently but simultaneously to swing probe 10 in an arc about axis Y—Y to effectuate the desired scan pattern. One preferred scan pattern is to oscillate arm 10B and probe 10 one complete cycle consisting of one clockwise sweep of 180 degrees plus one counterclockwise return sweep of 180 degrees about axis Y—Y for each single degree of rotation about axis Y—Y. This relationship is established and maintained while platform 81 rotates continuously.

Figure 12:
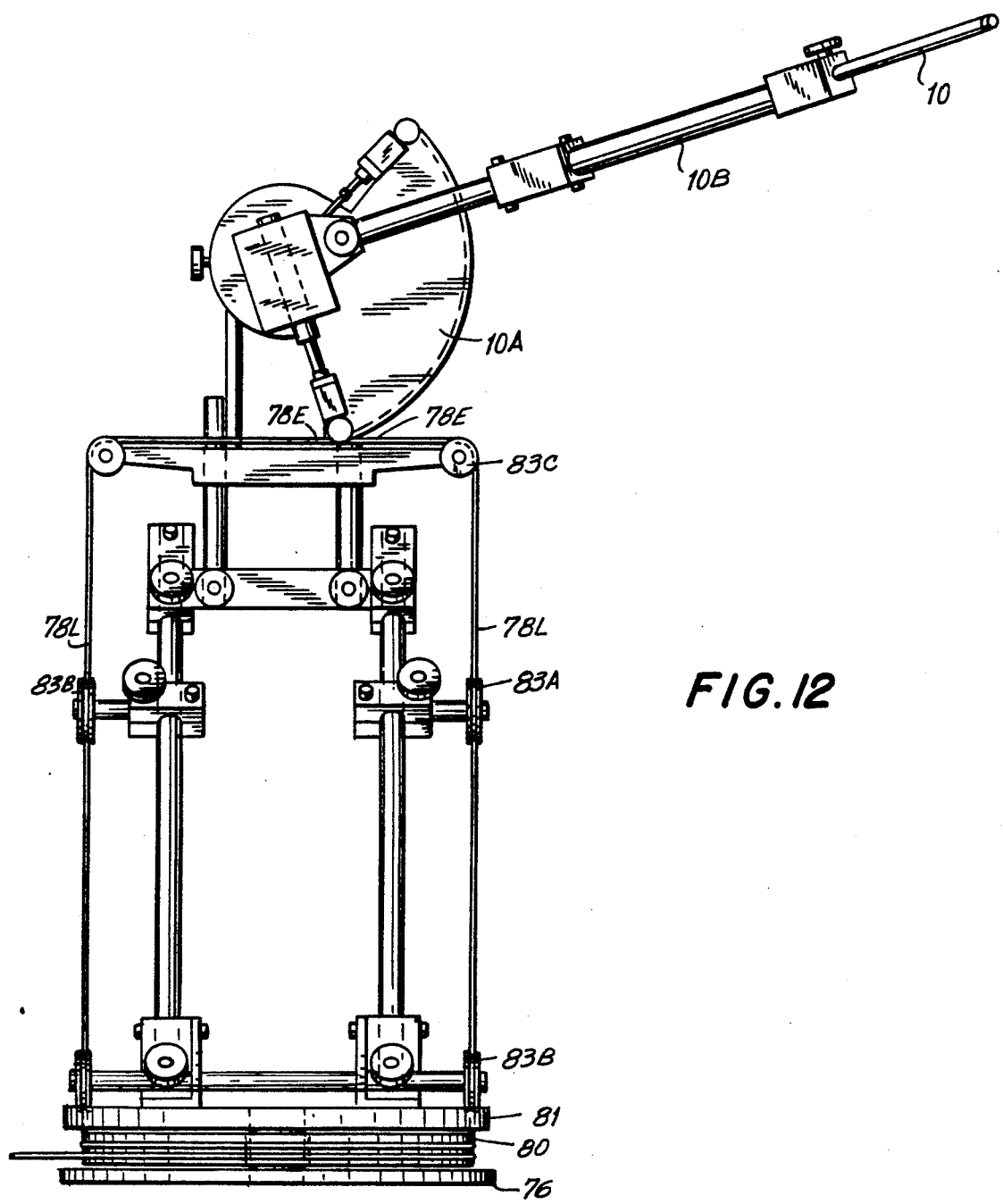
FIG. 12 is a front elevation view of the probe support arm as shown in FIGS. 1 and 5.

Now continuing with the description of the probe drive mechanism, FIGS. 5 and 12 show cable 78 to begin with disc segment 10A to which is mounted arm 10B that carries probe 10. The cable 78 defines a closed loop whose ends 78E are secured to opposite sides of segment 10A, thereby causing this segment and the probe to rotate about axis Y—Y when the cable moves in either of its opposite directions. The two legs 78L of cable 78 extend down tower 83 about idler pulleys 83A and 83B, and then around drum 80 which is freely rotatable as an idler about the X—X axis. Next cable 78 continues upward on tower 84 about idler pulleys 84C and 84C. One leg 78A of cable 78 extends upward through support 88 to idler pulley 91, while the other leg 78B of the cable extends through support 89 to drum 98.

To simplify the remaining description of the pulley and drum arrangement in FIGS. 8 and 9, shaft 86 will be considered forward of shaft 87, and drums and pulleys on these shafts will be described with respect to their respective forward and rearward parts.

As recited earlier leg 78A of the cable proceeds over the top and rearward on pulley 91 to, over the top and rearward on pulley 100 on shaft 87. Next 78A extends (in FIGS. 8) around pulley 108, then forward on the top of pulley 95, then down and around the front and upward on drum 92 in groove 93, then upward, atop and rearward of drum 92 to and under and rearward on drum 95, then upward around the back of drum 95, forward atop drum 95 to idler 107. Next 78A goes (in FIG. 8) rearward from idler 107 to the top and rearward on drum 98, and downward around the rear of drum 98 to and through support 89 where this becomes leg 78B of the cable for descent on stationary tower 84.

Rotation of motor shaft 87 drives sub-frame 102 which is keyed to shaft 87 to move identically with this shaft. Movement of sub-frame 102 about which cable 78 is partially wound causes the cable to move and therefor to drive the probe to rotate about its axis Y—Y. Since cable 78 extends around idler drum 80, probe 10 can be driven about axis Y—Y with no direct rotative affect on platform 81 and tower 83.

It is movement of tower 83 about the vertical axis, as driven by motor 70, which affects cable 78 running back to the drums 95, 98, and 100 on axle 87. In the present arrangement cable 78 extends to the probe most directly as cable legs 78A and 78B from idler drums 100 and 98 respectively. The winding of cable 78 in the opposite direction about bridge 102 and drums 95 and 92 is provided to accommodate and counteract the movement in cable 78 due to rotation of the platform 81 and attached tower 83. Alternative structures may be possible, but here the cable drive requires certain accommodation since the control system is stationary, while the driven section has complex movement.

Accordingly, when shaft 86 and drum 92 rotate, driving cable 74 and platform 81, cable 78 is also moved by virtue of the platform's movement, but the three free drums and keyed bridge 102 on axle 87 accommodate or counteract same, and cable 78 remains stabilized. The portion of cable 78 extending around drum 92 and pulley 95 causes pulley 95 to rotate thereby causing the cable 78 extending from pulley 95 around idler 107 and 108 and thereafter around pulleys 98 and 100 to also rotate. It should be noted that in this sequence pulley 95 rotates in the opposite direction from pulleys 98 and 100. Nevertheless this movement of shaft 86 merely causes pulleys 95 and 98 and 100 to rotate freely about shaft 87 and does not cause sub-frame 102 to move and therefore the probe does not move about axis Y—Y. Similarly movement of the sub-frame 102 due to motor 72 does not cause movement of shaft 85 or rotation of the platform about axis X—X. Stated differently, the object here is to impart to cable 78 the motion of cable 74 regardless of the independent motion of cable 78. This might not be necessary if cable 78 did not encircle drum 80, but in the embodiment illustrated such encirclement is very practical for ease and efficiency of cable placement.

It of course will be understood that other mechanical configurations for driving the probe about the equivalent movements with respect to the area plane may be utilized within the framework of the invention, however the probe drive mechanism 22 does include various novel features which are unique in mechanical movement with respect to ultrasonic probe devices and are worthy of particular attention.

With reference to appendix A, a complete mathematical derivation of the propagation of the surface wave mode is illustrated. In appendix B, a mathematical derivation of the equation giving the attenuation value due to scattering is presented. The analysis shows the independence of the phase for the attenuation of the signal and consequently only the amplitude measurement is required to derive the absorption characteristics. The absence of any factor other than pure amplitude loss in the final mathematic relationship expressed in equation no. B.11, appendix B, is theoretical proof of the advantageous nature derived from the use of surface wave acoustics, essential to the operation of the invention as described herein.

It will be further understood that the use of a cylindrical wave guide such as described herein, while preferred, is not essential as long as equivalent wave guide apparatus may be used to accomplish the surface wave mode. For example, U.S. Pat. No. 3,675,128 issued July 4, 1972 and U.S. Pat. No. 3,609,675 issued Sept. 28, 1978 both illustrate the use of a specific form of apparatus for generating surface waves in a microwave system.

Appendix A

The equations governing the propagation of sound in a loss less medium are $$\nabla^2 p - \frac{1}{a^2} \frac{\partial^2 p}{\partial t^2} ; \rho \frac{\partial \vec{u}}{\partial t} = -\nabla p \qquad A.1$$

where p is the pressure, $\vec{u}$ is the velocity vector, $\rho$ is the median density, a is the speed of sound and t is the time variable. Assume the harmonic solution $$p = P e^{i\omega t}; \vec{u} = \vec{U} e^{i\omega t} \qquad A.2$$

The pressure and velocity vector amplitudes $P, \vec{U}$ satisfy the equations $$\nabla^2 P + \frac{\omega^2}{a^2} P = 0; \vec{U} = -\frac{1}{i\omega\rho} \nabla P \qquad A.3$$

Figure 13:
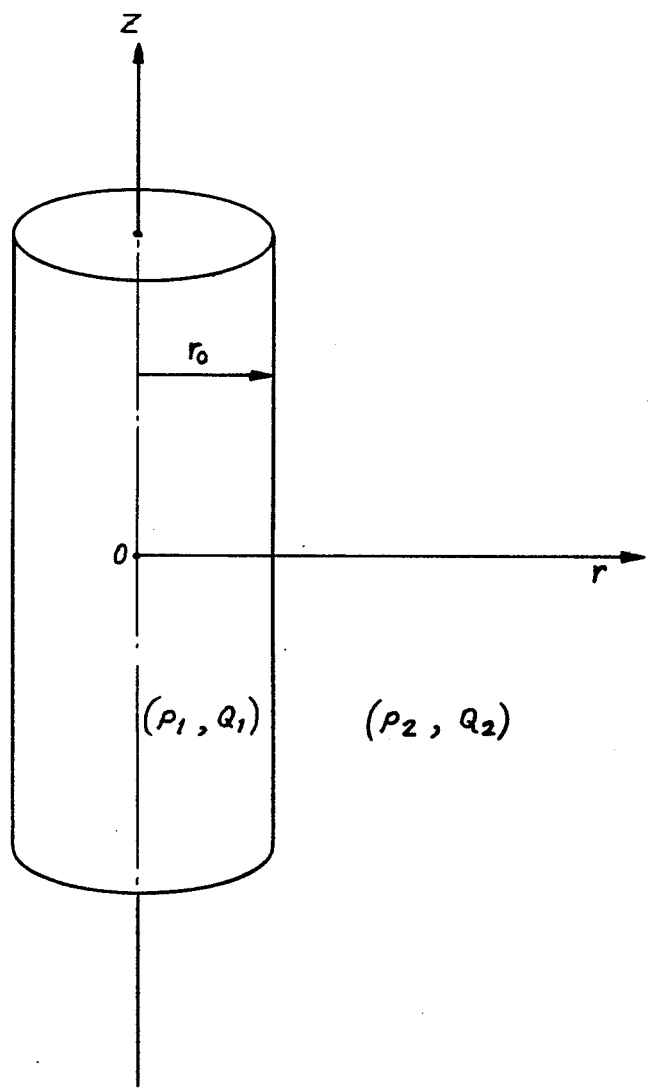
FIG. 13 is a schematic of the geometry of the cylinder illustrating the equations used herein.

In the cylindrical coordinates shown in FIG. 13, the first equation of system A.3 becomes $$\frac{1}{r} \frac{\partial}{\partial r} \left( r \frac{\partial P}{\partial r} \right) + \frac{\partial^2}{\partial z^2} P + \frac{\omega^2}{a^2} P = 0 \qquad A.4$$

where P is assumed to be independent of the angular coordinate. Assume the solution $$P = R e^{ik_z z} \qquad A.5$$

where R satisfies the equation $$\frac{1}{r} \frac{d}{dr} \left( r \frac{dR}{dr} \right) + k_r^2 R = 0 \qquad A.6$$

where $$k_r^2 + k_z^2 = \omega^2 / a^2 \qquad A.7$$

A solution of A.7 is $$R = C_0 (k_r r) \qquad A.8$$

where $$\begin{cases} C_0 = J_0(k_r r) & r \geq 0 \\ C_0 = H_0^{(2)} (k_r r) & r \neq 0 \end{cases} \qquad A.9$$

As indicated in FIG. 13, $J_o$, $H_o^{(2)}$ are the Bessel and Hankel functions respectively. Assume a rod of radius $r_o$ of a medium of density $\rho_1$ and speed of sound $a_1$ in a medium of density $\rho_2$ and speed of sound $a_2$. The radial component of the velocity vector is:

$$U_r = -\frac{1}{i\omega\rho} \frac{\partial P}{\partial r} = -\frac{k_r}{i\omega\rho} \frac{\partial P}{\partial (kr)} \qquad A.10$$

Thus for $r < r_0$ $$\begin{cases} P = P_1 J_0(k_1 r) e^{-ik_z z} \\ U_r = \frac{k_{1r} P_1}{i\omega\rho_1} J_1(k_1 r) e^{-ik_z z} \end{cases} \qquad A.11$$

and for $r > r_0$ $$\begin{cases} P = P_2 H_0^{(2)} (k_2 r) e^{-ik_z z} \\ U_r = \frac{k_{2r} P_2}{i\omega\rho_2} H_1^{(2)} (k_2 r) e^{-ik_z z} \end{cases} \qquad A.12$$

when $P_1$, $P_i$ are integration constants.

The boundary conditions at $r=r_o$ are the continuity of P and $U_r$. Thus $$\begin{cases} P_1 J_0(k_1 r_0) - P_2 H_0^{(2)}(k_2 r_0) = 0 \\ P_1 \dfrac{k_{1r}}{i\omega\rho_2} J_1(k_1 r_0) - P_2 \dfrac{k_{2r}}{i\omega\rho_2} H_1^{(2)}(k_2 r_0) = 0 \end{cases} \quad \text{A.13}$$

and the dispersion equation is $$\frac{k_1 r_0}{\rho_1} \frac{J_1(k_1 r_0)}{J_0(k_1 r_0)} - \frac{k_2 r_0}{\rho_2} \frac{H_1^{(2)}(k_2 r_0)}{H_0^{(2)}(k_2 r_0)} = 0 \quad \text{A.14}$$

write $$\phi_1 = k_1 r_0; \phi_2 = i k_2 r_0 \quad \text{A.15}$$

The dispersion equation becomes $$\frac{\phi_1}{\rho_1} \frac{J_1(\phi_1)}{J_0(\phi_1)} = -\frac{i\phi_2}{\rho_2} \frac{H_1^{(2)}(-i\phi_2)}{H_0^{(2)}(-i\phi_2)} \quad \text{A.16}$$

for $\phi_2$ real and positive, functions $$-H^{(2)}{}_1(-i\phi_2); i H^{(2)}{}_0(-i\phi_2) \quad \text{A.17}$$

are real and positive. For $\phi_2 \to 0$ one has $$\begin{cases} -i H_0^{(2)}(-i\phi_2) \sim +\dfrac{2}{\pi} \ln \dfrac{2}{\gamma\phi_2} \\ -H_1^{(2)}(-i\phi_2) \sim +\dfrac{2}{\pi} \ln \dfrac{1}{\phi_2} \end{cases} \quad \text{A.18}$$

For $\phi_2 \to \infty$ $$\begin{cases} -i H_0^{(2)}(-i\phi_2) \sim \dfrac{e^{-\phi_2}}{\sqrt{\dfrac{\pi}{2}\phi_2}} \\ -H_1^{(2)}(-i\phi_2) \sim \dfrac{e^{-\phi_2}}{\sqrt{\dfrac{\pi}{2}\phi_2}} \end{cases} \quad \text{A.19}$$

When $\phi_2$ is real and positive, Equation A.16 defines a surface wave mode. According to the asymptotic Equations A.19, the pressure field decays with an experimental-like low with the radial distance r as shown in the example of FIG. 1 and the pressure field configuration has the characteristic shown in FIG. 3. The phase velocity of the surface wave mode is:

$$V_f = \omega/k_z \quad \text{A.20}$$

Thus $$\phi_1^2 = \left(\frac{\omega}{a_1}\right)^2 \left(1 - \frac{a_1^2}{v_f^2}\right) r_0^2 \quad \text{A.21}$$

and

-continued $$\phi_2^2 = \left(\frac{\omega}{a_1}\right)^2 \left(\frac{a_1^2}{v_f^2} - \frac{a_1^2}{a_2^2}\right) r_0^2 \quad \text{A.22}$$

From A.21 and A.22 one has $$\frac{\omega r_0}{a_2} = \sqrt{\frac{\phi_1^2 + \phi_2^2}{\left(\dfrac{a_2}{a_1}\right)^2 - 1}} \quad \text{A.23}$$

and $$\frac{a_2}{v_f} = \sqrt{\frac{\phi_1^2 + \left(\dfrac{a_2}{a_1}\right)^2 \phi_2^2}{\phi_1^2 + \phi_2^2}} \quad \text{A.24}$$

Because $a_2 > a_1$ one has $a_2/v_f > 1$. Also $$\frac{a_1}{v_f} = \sqrt{\frac{\left(\dfrac{a_1}{a_2}\right)^2 \phi_1^2 + \phi_2^2}{\phi_1^2 + \phi_2^2}} \quad \text{A.25}$$

Thus the phase velocity of the surface wave mode is found in the range $$a_1 < v_f < a_2 \quad \text{A.26}$$

and $$\lim_{\omega \to 0} v_f = a_2 \quad \text{A.27}$$

In the low frequency limit one has from the dispersion equation $$\frac{k_1 r_0}{\rho_1} \frac{J_1(k_1 r_0)}{J_0(k_1 r_0)} \sim \frac{1}{\rho_2} \frac{1}{\ln \dfrac{2}{\gamma\phi_2}} \quad \text{A.28}$$

and $$k_1 r_0 = \phi_1 \sim \frac{\omega r_0}{a_1} \sqrt{1 - \left(\frac{a_1}{a_2}\right)^2} \quad \text{A.29}$$

$$\ln \frac{2}{\gamma\phi_2} \sim \frac{\rho_1}{\rho_2} \frac{J_0}{\phi_1 J_1} \quad \text{A.30}$$

Thus in the low frequency range the dispersion equation yields $$\frac{a_2}{v_f} \sim 1 + \frac{2}{\gamma^2} \left(\frac{a_2^2}{a_1^2} - 1\right) e^{-2 \frac{\rho_1}{\rho_2} \frac{J_0}{\phi_1 J_1} \frac{1}{\phi_1^2}} \quad \text{A.31}$$

where $$\gamma = 1.781 \quad \text{A.32}$$

Attenuation Due to Scattering Losses

Assume an element of volume $\delta V$ at a distance $r$ from the axis of the waveguide:

$$\delta V = r \delta r \delta \psi \delta z \quad \text{B.1}$$

Figure 14:
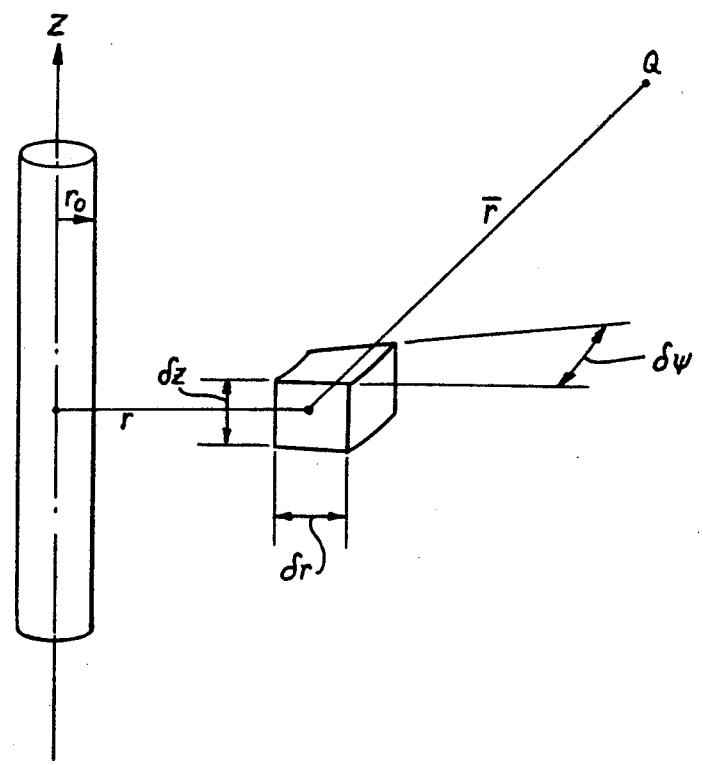
FIG. 14 is an illustration of the volume encompassing the compressibility factors herein.

As indicated in FIG. 14, the pressure amplitude of the pressure wave scattered by $\delta V$ is:

$$\delta P_{sc} \sim \frac{1}{2\pi^2} k_0^3 \, \delta V \, P\left(\frac{c}{c_0} - 1\right) \frac{e^{-ik_0 \bar{r}}}{k_0 \bar{r}} \quad \text{B.2}$$

where $c$ is the compressibility factor of the medium within $c_o$ is the average value of the compressibility factor of the medium outside the waveguide. $P_i$ is the pressure of the surface wave mode at the position of element of volume $\delta V$. The overall pressure $P_{sc}$ generated at a point Q by the distribution of scatterers surrounding the waveguide is:

$$P_{sc} = \frac{1}{2\pi^2} k_0^3 \int\!\!\int\!\!\int r P_i \left(\frac{c}{c_0} - 1\right) e^{\frac{-ik_0\bar{r}}{k_0\bar{r}}} dr d\psi dz \quad \text{B.3}$$

where $\bar{r}$ is the distance between Q and $\delta V$ and c is a function of position. At very large distances $P_{sc}$ becomes $$P_{sc} = \frac{k^2_0}{2\pi^2 r_o} \int\!\!\int\!\!\int r P_i \left(\frac{c}{c_o} - 1\right) e^{-ik_0\bar{r}} dr d\psi dz \quad \text{B.4}$$

The radial component of the velocity vector generated by the scattering element of volume $\delta V$ is $$\delta U_{rsc} \sim \frac{1}{2\pi^2} k_o^3 \, \delta V P_i \frac{1}{\alpha_o \rho_o}\left(\frac{c}{c_o} - 1\right)\left(1 + \frac{1}{ik_o\bar{r}}\right) e^{\frac{-ik_o\bar{r}}{k_o\bar{r}}} \quad \text{B.5}$$

and the total value of $U_{rs}$ over the sphere of radius $r_s$, for very large values of $r_s$ is:

$$U_{rsc} \sim \frac{k_o^2}{2\pi^2 r_s} \frac{1}{\alpha_o \rho_o} \int\!\!\int\!\!\int r P_i \left(\frac{c}{c_o} - 1\right) e^{-ik_o\bar{r}} dr d\psi dz \quad \text{B.6}$$

Thus the total scattered acoustic power is $$W_{sc} = \tfrac{1}{2} \int\!\!\int P_{sc} U^*_{rsc} r_s^2 \sin\sigma d\sigma d\psi \quad \text{B.7}$$

when $U^*_{rsc}$ denotes the complex conjugate of $U_{rsc}$. $W_{sc}$ is independent of $r_s$.

The phase of both $P_{sc}$, $U_{rsc}$ is dictated by the local value of $P_i$, which is the pressure value of the surface wave mode, i.e.

$$P_i = P_2 H_0^{(2)}(k_2 r) e^{-ik_z z} \quad \text{B.8}$$

The acoustic power associated with the surface wave mode is:

$$W_i = \tfrac{1}{2} \int\!\!\int r P_i U_z^* dr d\psi = \pi \int_0^\infty r P_i U_z^* dr \quad \text{B.9}$$

where $U^*_z$ denotes the complex conjugate of the z-component of the velocity vector of the surface wave mode. The z-component $U_z$ is given by:

$$U_z = -\frac{1}{i\omega\rho} \frac{\partial p}{\partial z} = \frac{k_z}{\omega\rho} P_2 H_0^{(2)}(k_2 r) e^{-k_z z} \quad \text{B.10}$$

Thus the total attenuation suffered by the surface wave mode over the length $z_0$ of the waveguide is given by $$\int_0^{z_2} \alpha dz = \frac{1}{2\pi} \lg_{10}\left(1 - \frac{W_s}{W_i}\right) \quad \text{B.11}$$

where $\alpha$ is the local attenuation coefficient due to scattering losses. This equation is valid as long as $W_s << W_i$. In conclusion for small losses, the phase of the incident surface wave mode is not altered and the measurement of the attenuation suffered along the waveguide is related to the sum of the losses suffered at each section of the waveguide.

What is claimed is:

1. An ultrasound diagnostic device for examining a subject comprising
   an elongated ultrasonic probe including means for repeatedly propagating and constraining ultrasonic surface waves along the length of said probe in a direction such that the evanescent pressure field penetrates said subject in a direction orthogonal to said surface wave,
   means for moving said ultrasonic probe about said subject along a plurality of orientations for passing said evanescent pressure field through said subject along said plurality of orientations,
   means for detecting the loss of energy in each evanescent pressure field resulting from absorption by said subject during each successive propagation, and
   means for processing and correlating each successive detected loss of energy in each propagation for producing a computed tomographic image of a defined plane through said subject.

2. The device of claim 1 wherein said probe comprises a cylindrical wave guide, containing a first liquid and a transducer, oriented to propagate a surface wave within the cylinder, said probe being immersed within a second liquid, the speed of sound in said first liquid being slower than the speed of sound in said second liquid, said subject being placed in said second liquid.

3. The device of claim 1 wherein said probe is completely contained within an enclosure and wherein said subject penetrates said enclosure to a depth sufficient to penetrate said evanescent field.

4. The device of claim 1 wherein said probe is constrained along said plurality of orientations by means of a dual arm drive contained within an enclosure along with said probe.

5. The device of claim 1 wherein said probe is an elongated cylinder having a transducer at one end thereof and a reflector at the other end thereof, said probe containing a liquid having a speed of sound lower than the speed of sound in the medium surrounding said probe, thereby constraining propagation in said probe along the length of said probe toward said reflector, and back toward said transducer, thereby causing said evanescent field to penetrate said subject area twice.

6. The device of claim 1 wherein said probe is supported by an elongated arm for rotating said probe about said subject over an arc, said elongated arm being rotatable about a center line through said subject, means for moving said arm to describe a first complete arc about said subject, and means for rotating said elongated arm about said centerline by an incremental amount to reposition said probe for describing a second and additional arcs until a complete scan of said subject is achieved.

7. An ultrasound diagnostic device for examining a subject comprising an enclosure penetratable by said subject, said enclosure containing a first liquid having a first speed of sound characteristic, and an ultrasonic cylindrical probe containing an ultrasound transducer, said probe containing a second liquid having a second speed of sound characteristic which is higher than said first speed characteristic, said ultrasound transducer producing an ultrasound wave which is constrained within said probe such that only the evanescent field of said surface wave penetrates said subject, and means responsive to the energy loss in said ultrasound wave to provide an indication of absorption by said subject, said energy loss being represented by a pure amplitude loss.

8. The device of claim 7 wherein said means responsive to the energy loss is an amplitude detector, said detector responsive to the initial amplitude and the measured amplitude to provide a measure of amplitude loss corresponding to said energy loss.

9. The device of claim 7 wherein said probe is respositioned along a plurality of individual paths defining a plurality of planes through said subject, means responsive to the total energy loss along each orientation for calculating the individual absorption of a plurality of points over each plane, and means for contrastingly displaying said individual absorptions on each of said planes.

10. The device of claim 7 wherein said probe is completely contained within an enclosure and wherein said subject penetrates said enclosure to a depth sufficient to penetrate said evanescent field.

11. The device of claim 7 wherein said probe is constrained along said plurality of orientations by means of a dual arm drive contained within an enclosure along with said probe.

12. The device of claim 7 wherein said probe is supported by an elongated arm for rotating said probe about said subject over an arc, said elongated arm being rotatable about a center line through said subject, means for moving said arm to describe a first complete arc about said subject, and means for rotating said elongated arm about said centerline by an incremental amount to reposition said probe for describing a second and additional arcs until a complete scan of said subject is achieved.

13. A process for ultrasound diagnosis comprising the steps of positioning a subject proximate an ultrasound probe, propagating a plurality of ultrasound surface waves constrained within said probe and its evanescent field penetrating said subject, and measuring the amplitude loss in said surface wave after traversal of said probe, said amplitude loss being a measure of subject area absorption of energy from said evanescent field, anomalies within said subject area material representing higher absorption than non-anomalous material.

14. The process of claim 1 wherein said plurality of ultrasound surface waves are propagated along a plurality of orientations with respect to said subject area.

15. A device according to claim 6 and operable with a tank containing a quantity of fluid medium wherein said means for moving said probe within said fluid about said subject comprises:
a—a base positionable in said tank,
b—a platform rotatable on said base about a vertical axis x—x,
c—a first tower extending upward from and carried by said platform,
d—an arm carrying said probe and pivotable on said tower about a horizontal axis y—y,
e—a drive sub-assembly including first and second electric motor means fixedly situated outside said fluid, said first and second motor means being independent of each other,
f—first coupling means interconnecting said first motor means with said platform for rotating same about said x—x axis, and
g—second coupling means interconnecting said second motor with said arm for rotating same about said y—y axis.

16. A device according to claim 15 wherein said first and second coupling means each comprise a flexible cable.

17. A device according to claim 15 wherein said means for moving said probe further comprises at least a first drum freely rotatable on said base, said platform being fixed to rotate with said first drum, whereby said first coupling means engages and rotates said first drum, platform, tower and probe.

18. A device according to claim 17 further comprising a second drum freely rotatable on said base, said second coupling means engaging said second drum and thence extending to said arm, whereby said first and second coupling means remain and move together when said arm and probe are moved.

19. A device according to claim 16 further comprising adjustment means for imparting the motion of the first motor on the second cable, independent of motion of the second motor on said second cable.

* * * * *